US00PP30751P3

(12) United States Plant Patent
Olesen

(10) Patent No.: US PP30,751 P3
(45) Date of Patent: Jul. 30, 2019

(54) ***ROSA* HYBRID VARIETY PLANT DENOMINATED 'POULREN026'**

(50) Latin Name: ***Rosa* hybrid**
Varietal Denomination: Poulren026

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/731,967

(22) Filed: Sep. 5, 2017

(65) Prior Publication Data

US 2019/0075697 P1 Mar. 7, 2019

(51) Int. Cl.
*A01H 5/02* (2018.01)
*A01H 6/74* (2018.01)

(52) U.S. Cl.
USPC ..... Plt./136
CPC ..... *A01H 6/749* (2018.05)

(58) Field of Classification Search
USPC ..... Plt./136
See application file for complete search history.

(56) References Cited

PUBLICATIONS

UPOV hit on Tea rose plant named 'Poulren026', QZ PBR 49233, filed Sep. 19, 2016.*

* cited by examiner

*Primary Examiner* — Anne Marie Grunberg

(57) ABSTRACT

A new garden rose plant of the Hybrid Tea class which has abundant, pink apricot blend flowers and attractive foliage. This new and distinct variety has shown to be uniform and stable in the resulting generations from asexual propagation.

3 Drawing Sheets

Botanical designation: *Rosa* hybrid.
Variety denomination: 'Poulren026'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulren026', originated as a single seedling from the stated cross.

The new variety may be distinguished from its male pollen parent and female seed parent primarily by the following characteristics. The male pollen parent plant has an overall growth height of 45 cm while the new variety has an overall growth height of about 70 cm. The female seed parent plant has pure pink flowers while the new variety has pink apricot blend flowers.

The objective of the hybridization of this rose variety was to create a new and distinct variety with unique qualities, such as:

1. Uniform and abundant pink apricot blend flowers;
2. Vigorous, but compact growth when propagated on its own roots;
3. Exceptional disease resistance;
4. Fragrant flowers.

This combination of qualities is not present in previously available commercial cultivars of this type, known to the inventor, and distinguish 'Poulren026' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulren026' was selected in the spring of 2008 by the inventor as a single plant from the progeny of the aforementioned hybridization.

Asexual reproduction of 'Poulren026' by rooted cuttings was first done by Mogens N. Olesen in the nursery in Fredensborg, Denmark in July, 2008. This initial and other subsequent asexual propagations conducted in controlled environments have demonstrated that the characteristics of 'Poulren026' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren026'.

Specifically illustrated in FIG. 1 of the drawings is an open flower.

DETAILED DESCRIPTION OF THE VARIETY

Figure 1:
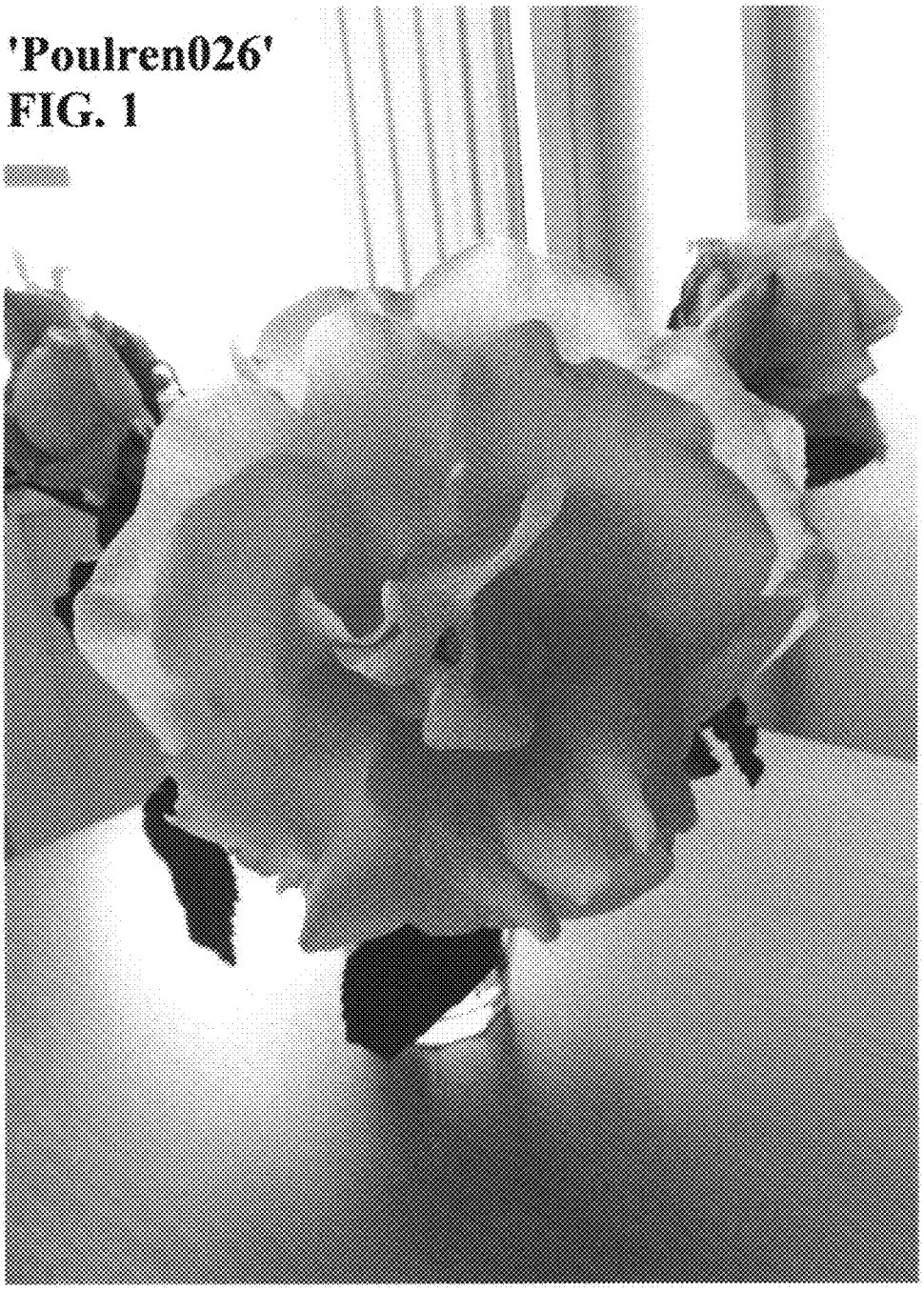
Figure 2:
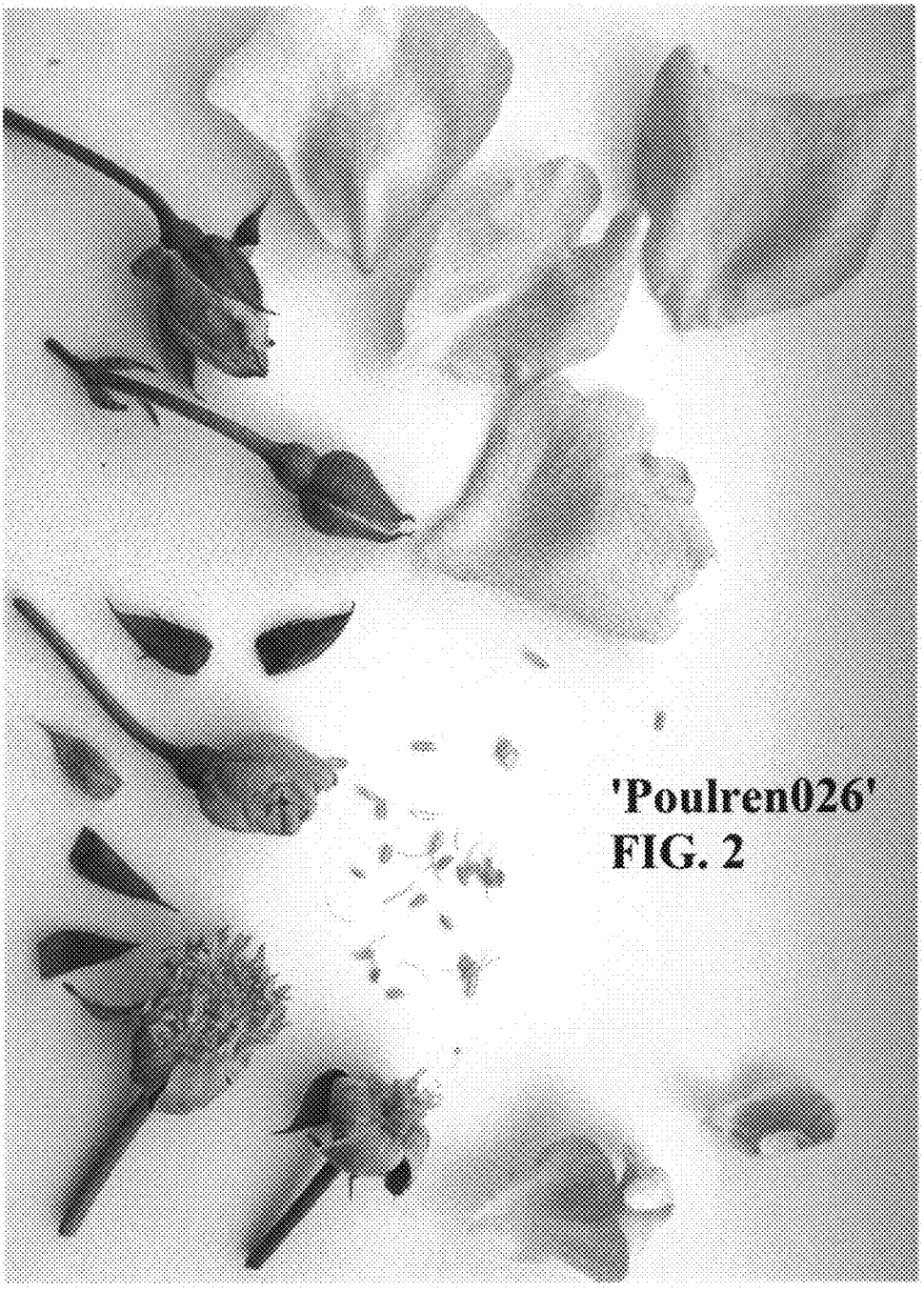
FIG. 2 shows flower petals detached, sepals detached, receptacle shape, and reproductive flower parts.
Figure 3:
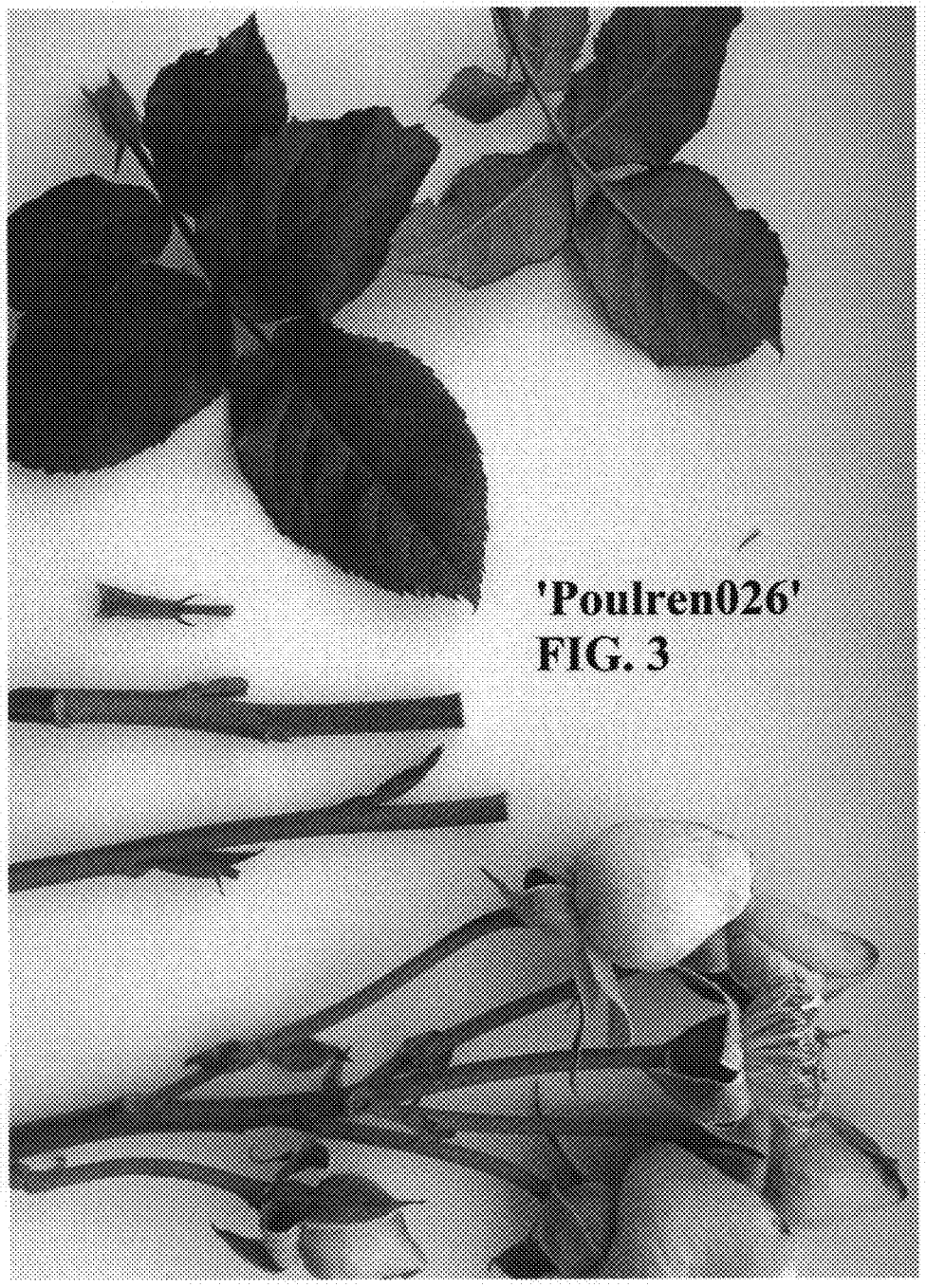
FIG. 3 shows leaves, bare stems, and a cluster of flower buds. Plants shown are 1 years of age.

The following is a description of 'Poulren026', as observed in its growth in a field nursery in Odense Denmark.

Observed plants are 1 year of age, and were grown on their own roots. Color references are made using The Royal Horticultural Society (London, England) Colour Chart, 2001, except where common terms of color are used.

For a comparison, several physical characteristics of the rose variety 'Poulnap002', U.S. Plant Pat. No. 25,169 are compared to 'Poulren026' in Chart 1.

CHART 1

| | 'Poulren026' | 'Poulnap002' |
|---|---|---|
| Petal Count | About 20 petals | 50 petals |
| Flower Diameter | 90 to 100 mm | 120 mm |
| General Tonality of Flower Color | Red Group 49A | Red Group 43C |

Flower and flower bud:

*Blooming habit*.—Continuous.

*Flower bud*.—Size: Upon opening, 35 mm in length from base of receptacle to end of bud. Bud diameter is 15 mm. Bud form: Ovoid. Bud color: As sepals divide petals are Red Group 37B. Sepal inner surface: Color: Green Group 138B. Surface: Lightly pubescent. Sepal outer surface: Color: Green Group 138A with intonations of Greyed-Purple Group 180A. Texture: Smooth. Sepal Shape: Apex: Cirrhose. Base: Flat at union with receptacle. Sepal Margin: Margins have weak foliaceous appendages on three of the five sepals. Sepal size: 25 mm long, 10 mm wide. Receptacle: Texture: Smooth. Size: mm in height, mm wide. Color: Yellow-Green Group 144A. Shape: Campanulate. Pedicel: Surface: Smooth. Length: 50 to 65 mm. Diameter: 3 to 4 mm. Color: Yellow-Green Group 144A. Strength: Weak. Peduncle: Length: 10 to 30 cm. Diameter: 3 to 4 mm. Color: Yellow-Green Group 144A. Texture: Smooth.

*Flower bud development*.—Flower buds are borne in clusters of 5 to 7 flower buds per stem in corymb form.

*Flower bloom*.—Fragrance: Strong perfume. Duration: The blooms have a duration on the plant of approximately 10 days. Petals fall cleanly away from plant after flowers have fully matured. Size: Flower diameter is 90 to 100 mm when open. Flower depth is 50 mm. Flower shape: Open cup, semi-double flower, with petals that curve out from the center. Shape of flower, side view: The upper portion is a flattened convex. The lower portion is a flattened convex.

*Petalage*.—Under normal conditions, flowers have about 20 petals.

*General tonality of flower*.—Open flowers are Red Group 49A.

*Petal color*.—Upon opening, outer petals Upper surface: Red Group 49B. Lower surface: Red Group 49A. Upon opening, inner petals: Upper surface: Red Group 50C. Lower surface: Red Group 49B. Basal petal spots, upon opening: Upper surface: Yellow Group 10A. Lower surface: Yellow Group 10C. After opening, outer petals Upper surface: Red Group 51D. Lower surface: Red Group 49C. After opening, inner petals: Upper surface: Red Group 49B. Lower surface: Red Group 49C. Basal petal spots, after opening: Upper surface: Yellow Group 10A. Lower surface: Yellow Group 10C.

*Petals*.—Petal Reflex: Moderate. Margin: Entire and uniform, with occasional single or multiple clefts. Moderate undulations. Shape: Broad and elliptic. Apex shape: Emarginate. Base shape: Acute. Size: 70 mm (l)×70 mm (w). Texture: Slightly textured. Thickness: Average.

*Petaloids*.—Size: 20 to 50 mm (l) by 22 to 45 mm (w). Quantity: About 3. Shape: Irregular, with an acute base and rounded apex. Color: Upper surface is Red Group 49B. Lower surface is Red Group 49C. Basal petaloid spots, after opening are Yellow Group 10A on the upper surface and Yellow Group 10C on the lower surface.

*Reproductive flower parts*.—Pollen: None observed. Anthers: Size: 4 mm in length. Color: Yellow Group 13A. Quantity: 160 on average. Filaments: Color: Yellow Group 13C. Length: 12 mm. Pistils: Length: 5 to 10 mm. Quantity: 100 on average. Stigmas: Color: Green Yellow Group 1D. Styles: Color: Red-Purple Group 73A and Green Yellow Group 1D. Location of stigmas: Inferior in location relative to the length of the filaments and the height of the anthers. Hips: None Observed.

Plant:

*Plant growth*.—Upright, bushy. Plants are about 70 cm in height, and 65 cm wide.

*Stems*.—Color of mature growth: Yellow-Green Group 146A. Length: Canes are 60 to 70 cm from the base of the plant to the flowering portion. Diameter: 8 to 10 mm. Internodes: On mature canes 15 to 40 mm between nodes. Surface Texture: Young wood: Smooth. Older wood: Smooth.

*Long prickles*.—Incidence: Low, 1 prickle per 10 cm of stem. Size: Average length of prickles on mature stems is 5 mm. Shape: Upper portion is linear. Lower portion is concave. Color: Juvenile prickles: Greyed-Red Group 180A. Mature prickles: Greyed-Red Group 180B.

*Plant foliage*.—Compound leaf: 100 to 140 mm (l)× 100 to 120 (w). Quantity: About 3 leaves per 10 cm of stem on average. Color of mature foliage: Upper side: Yellow-Green Group 147A. Lower side: Yellow-Green Group 147B.

*Plant leaves and leaflets*.—Stipules: Size: 25 mm long, 6 mm wide. Quantity: 2 per compound leaf. Shape: Linear, slightly broad based with outward extending apices. Margins: Finely serrated. Color: Yellow-Green Group 147A. Petiole: Length: About 15 mm. Diameter: 2 mm. Upper surface color: Yellow-Green Group 147A with intonations of Greyed-Purple Group 183A. Lower surface color: Yellow-Green Group 144A. Rachis: Length: About 25 mm. Upper surface color: Yellow-Green Group 147A with intonations of Greyed-Purple Group 183A. Lower surface color: Yellow-Green Group 144A. Leaflet: Quantity: Normally 5 leaflets. Margins: Serrated. Size: Terminal leaflets are about 50 to 75 mm long, and 25 to 50 mm wide. Shape: Generally elliptical. Base: Rounded. Apex: Acuminate to mucronate. Texture: Somewhat rugose. Thickness: Average. Arrangement: Odd pinnate. Venation: Reticulate. Glossiness: Moderately glossy.

*Disease resistance*.—Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

*Cold hardiness*.—The variety is tolerant to USDA Cold Hardiness Zone 6.

*Heat tolerance*.—The variety has been found to be suitable for climate conditions found in the American Horticulture Society heat zone 7.

I claim:

1. A new and distinct variety of rose plant of the Hybrid Tea rose class named 'Poulren026', substantially as illustrated and described herein, due to its abundant pink apricot blend flowers, disease resistance, and extended period of bloom.

* * * * *

'Poulren026'

'Poulren026'

'Poulren026'